(12) United States Patent
Altman

(10) Patent No.: US 6,834,652 B2
(45) Date of Patent: Dec. 28, 2004

(54) CATHETER PROTECTIVE SHIELD

(75) Inventor: Sanford D. Altman, Miami Beach, FL (US)

(73) Assignee: SDA Product, Inc., North Miami Beach, FL (US)

( * ) Notice: Subject to any disclaimer, the term of this patent is extended or adjusted under 35 U.S.C. 154(b) by 0 days.

(21) Appl. No.: 09/941,012

(22) Filed: Aug. 28, 2001

(65) Prior Publication Data

US 2003/0221693 A1 Dec. 4, 2003

(51) Int. Cl.$^7$ ................................................ A61F 13/00
(52) U.S. Cl. ......................... 128/846; 128/877; 128/888
(58) Field of Search ................................ 128/846, 877, 128/878, 888, 879, 849–856; 604/174, 180, 332, 334, 336, 347–353, 355, 357

(56) References Cited

U.S. PATENT DOCUMENTS

| | | | |
|---|---|---|---|
| 3,568,675 A | * | 3/1971 | Harvey .................... 604/355 |
| 3,667,469 A | | 6/1972 | Marsan |
| RE29,319 E | * | 7/1977 | Nordby .................... 604/355 |
| 4,221,215 A | | 9/1980 | Mandelbaum |
| 4,324,237 A | | 4/1982 | Buttaravoli |
| 4,519,793 A | | 5/1985 | Galindo |
| 4,636,206 A | | 1/1987 | Ederati et al. |
| 4,969,880 A | | 11/1990 | Zamierowski |
| 5,074,847 A | | 12/1991 | Greenwell et al. |
| 5,090,406 A | | 2/1992 | Gilman |
| 5,181,274 A | | 1/1993 | DeFiore |
| 5,263,922 A | | 11/1993 | Sova et al. |
| 5,336,204 A | | 8/1994 | Matyas |
| 5,383,893 A | | 1/1995 | Daneshvar |
| 5,415,642 A | * | 5/1995 | Shepherd .................... 604/344 |
| 5,478,333 A | | 12/1995 | Asherman, Jr. |
| 5,495,856 A | | 3/1996 | Fentress |
| 5,605,534 A | | 2/1997 | Hutchison |
| 5,605,546 A | | 2/1997 | Wolzinger et al. |
| 5,690,622 A | * | 11/1997 | Smith et al. ................. 604/333 |
| 5,720,713 A | | 2/1998 | Hutchison |
| 5,807,341 A | | 9/1998 | Heim |
| 5,823,977 A | | 10/1998 | Dalyea |
| 5,834,093 A | | 11/1998 | Challis et al. |
| 5,843,049 A | | 12/1998 | Heilmann et al. |
| 5,885,254 A | | 3/1999 | Matyas |
| 6,095,996 A | | 8/2000 | Steer et al. |
| 6,117,111 A | | 9/2000 | Fleischmann |
| 6,124,521 A | | 9/2000 | Roberts |
| 6,222,090 B1 | | 4/2001 | Weston |
| 6,267,115 B1 | | 7/2001 | Marshel |
| 6,276,364 B1 | | 8/2001 | Warner |
| 2001/0001110 A1 | | 5/2001 | Bodenschatz et al. |
| 2001/0025153 A1 | | 9/2001 | Groitzsch et al. |
| 2001/0034505 A1 | | 10/2001 | Wilke |
| 2001/0056262 A1 | | 12/2001 | Cabiri et al. |
| 2002/0065505 A1 | | 5/2002 | Willemstyn |
| 2002/0103450 A1 | | 8/2002 | Corrales |
| 2002/0107466 A1 | | 8/2002 | Faasse, Jr. |
| 2002/0123710 A1 | | 9/2002 | Worthley |

FOREIGN PATENT DOCUMENTS

| | | |
|---|---|---|
| EP | 0 671 182 | 9/1995 |
| GB | 1 457 164 A | 12/1976 |

* cited by examiner

*Primary Examiner*—Michael A. Brown
(74) *Attorney, Agent, or Firm*—Saliwanchik, Lloyd & Saliwanchik

(57) ABSTRACT

This subject invention is a protective shield for protecting indwelling medical devices, during showering, bathing, or swimming. This protective shield includes an inner bag having an opening containing by a medical grade absorbent material, where the opening is surrounded by a medical grade adhesive for attachment to a patient's skin. The medical device in inserted into the bag through the absorbent material. This bag is covered by an attached outer cover, which has an adhesive material applied along it peripheral edge or attachment to the patient, which diverts the flow of fluid away from the opening of the inner bag. The absorbent material in opening of the inner bag traps and hold fluid penetrating the two adhesive barriers affording additional level of protection in preventing fluid from reaching the inside of the pouch.

16 Claims, 7 Drawing Sheets

CATHETER PROTECTIVE SHIELD

FIELD OF THE INVENTION

The present invention relates to a protective device for a catheter and or device that transcends from the outside of the body to the inside of the body, and more particularly to a protective device which decreases the amount of foreign material (fluid and/or debris) presented to the catheter and its corresponding exit site, decreasing the risk of foreign material reaching the inside of the body.

BACKGROUND OF THE INVENTION

With the improvement in healthcare over the last several decades, there is an increasing number of patients living with indwelling catheters traveling from the inside to the outside of their bodies. These catheters are being used for a variety of reasons such as dialysis, chemotherapy, alimentation, and fluid drainage, to name a few. The protection of the catheter and corresponding exit site is a significant concern for these patients, as moisture or other material can support the growth of harmful or infectious bacteria in and around the exit site.

As such, these patients ability to perform normal daily activities, such as swimming, bathing, and even showering is severally limited, and can even become prohibited for many of the patients. As a result, even when the patient begins to recover, the catheter becomes a constant reminder of their illness.

Accordingly, there remains a need for a device for protecting a catheter and corresponding exist site during such activities as swimming, bathing, or showering.

BRIEF SUMMARY OF THE INVENTION

The protective shield of the subject invention provides a means for protecting an indwelling catheter and corresponding exit site from dirt, debris, and moisture. The protective shield comprises a pair of protective layers, an inner bag and an outer cover. The inner bag is designed for receiving the proximal end of the catheter, having a front side and a backside, with the front side having an opening therethrough. Positioned and affixed within the front side opening is a moisture absorbent material, where the moisture absorbent material comprises a substantially centrally positioned slit therethrough. The inner bag further comprises a moisture resistant adhesive material suitable for application to the patient's skin, where the adhesive material is applied to the outer surface of the front side of the inner bag, substantially surrounding the opening without discontinuity, such that a protective seal can be formed when the inner bag is applied to the patient's skin.

The outer cover comprises a sheet of flexible, fluid-impermeable material having a peripheral edge that adheres to the patients skin, surrounding the inner bag. A moisture resistant adhesive material suitable for application to the patient's skin is applied to the peripheral edge without discontinuity, such that a protective seal can be formed when the outer cover is applied to the patient's skin. The outer cover is sized such that the inner bag is encompassed within the peripheral edge. The outer cover serves as a tarp to move water away from the inner bag.

In use, a catheter is inserted into the inner bag by inserting the catheter though the slit in the absorbent material. The catheter is drawn into the bag until the absorbent material abuts the catheter exit site and surrounding area. The inner bag is secured in position by the adhesive material in contact with the patient's skin. The outer cover is positioned over the inner bag, such that the inner bag is positioned within the peripheral edges of the outer cover. The outer cover is secured in position by the adhesive material in contact with the patient's skin. The bag can be removed by peeling the outer cover from the patient's skin. The inner bag is gently peeled from the patient's skin and the catheter removed from the bag. The protective shield is then discarded.

An advantage of this invention is that the shield decreases the risk of foreign material reaching the inside of the body.

These and other objects, features and advantages of the present invention will be more readily understood with reference to the following detailed description, read in conjunction with the accompanying drawing figures.

All patents, patent applications and publications referred to or cited herein, or from which a claim for benefit of priority has been made, are incorporated by reference in their entirety to the extent they are not inconsistent with the explicit teachings of this specification, including: U.S. Pat. No. 4,415,642 to Shepherd, U.S. Pat. No. 4,5,495,856 to Fentress, and U.S. Pat. No. 6,222,090 to Weston.

DETAILED DISCLOSURE OF THE INVENTION

The protective shield 10 of the subject invention provides a means for protecting an indwelling catheter and corresponding exit site from dirt, debris, and moisture.

Figure 1:
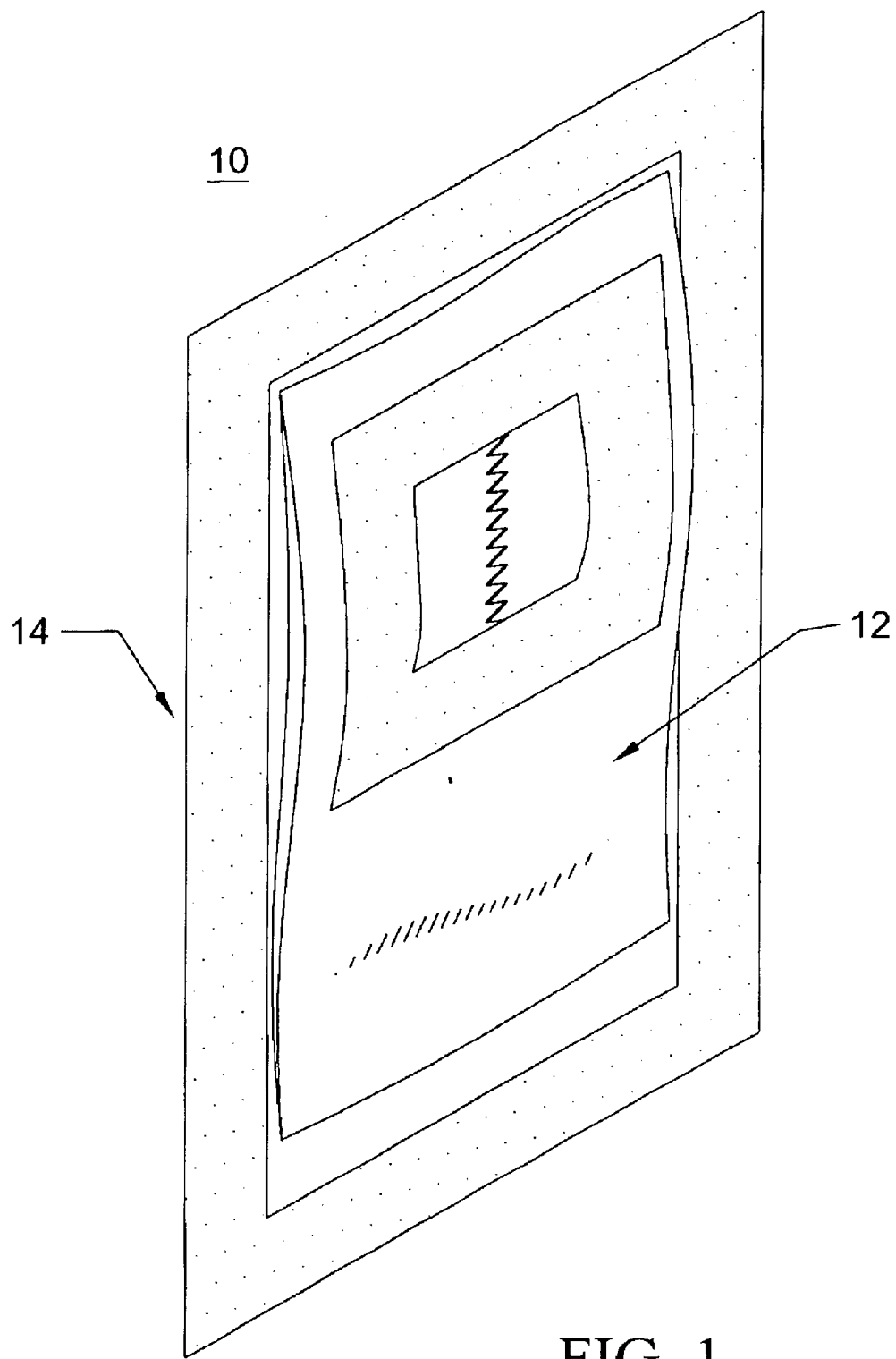
FIG. 1 depicts a perspective view of the catheter protective shield.
Figure 2:
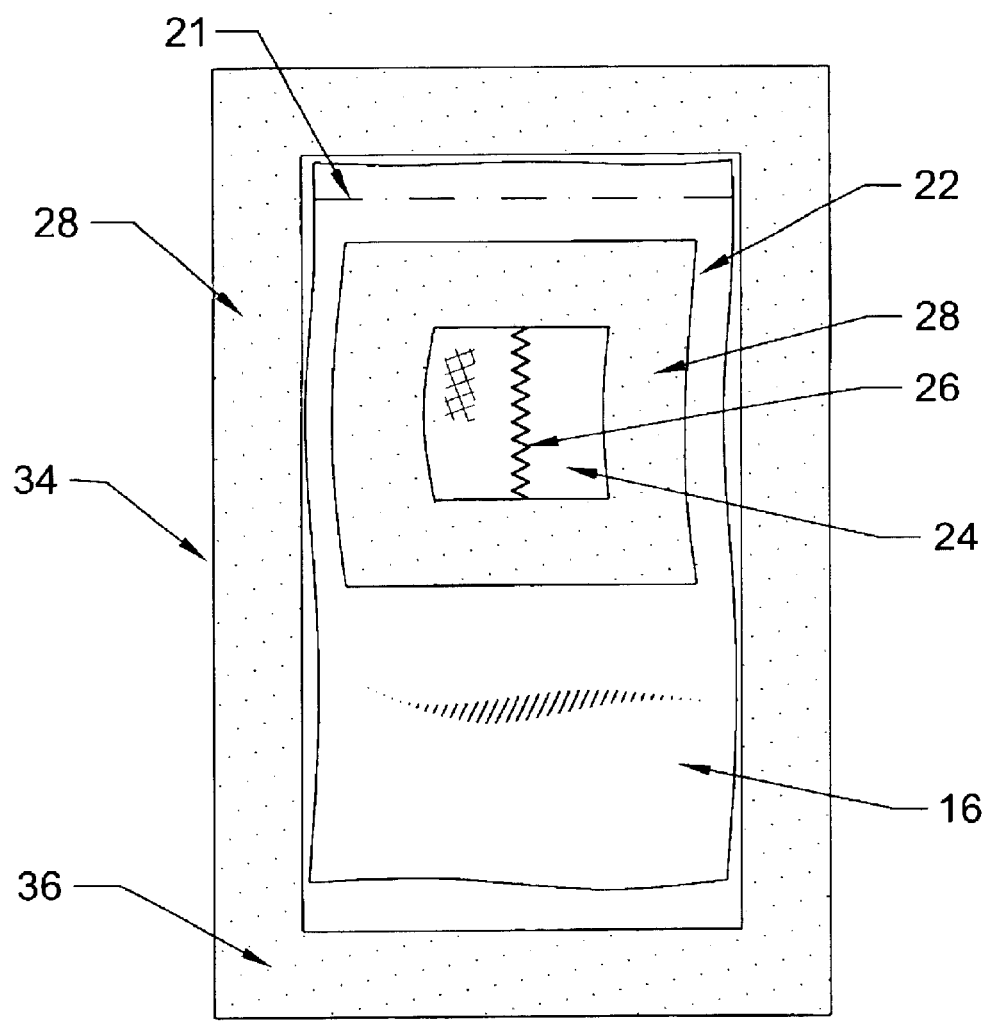
FIG. 2 depicts a front view of the catheter protective shield.
Figure 5:
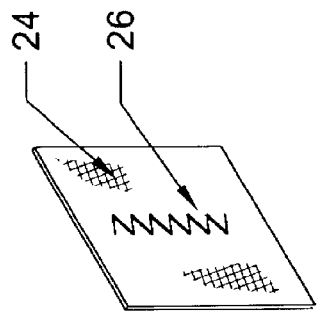
FIG. 5 depicts a perspective view of the absorbent material.
Figure 4:
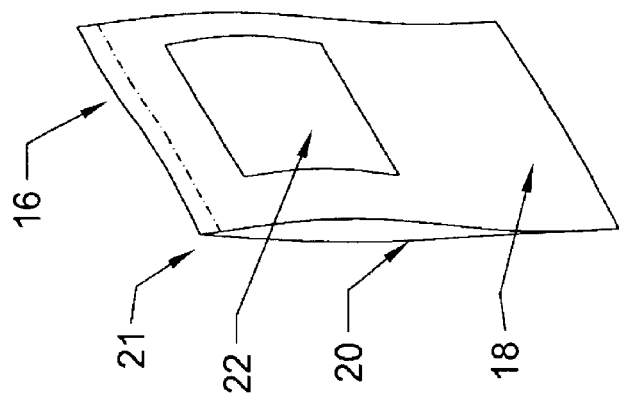
FIG. 4 depicts a perspective view of the inner bag.

In an embodiment, as shown in FIGS. 1–2, the protective shield 10 of the subject invention comprises a first protective layer 12 and a second protective layer 14. The first 12 and second protective layers 14 are made from a flexible, fluid-impermeable material capable of conforming to a patient's skin, including, but not limited to plastic, polymer, latex, or rubber. Additionally, it is desirable that the material be substantially impervious to bacterium, fungi, viruses, and other infectious agents.

As shown in FIGS. 4–6 and 9, the first protective layer 12 comprises an inner bag 16 for receiving the proximal end 51 of the catheter 50, having a front side 18 and a backside 20, where the front side 18 has an opening 22 therethrough. Positioned and affixed within the front side opening 22 is a moisture absorbent material 24, where the moisture absorbent material 24 comprises a substantially centrally positioned slit 26 therethrough. The moisture absorbent material 24 can comprise conventional absorbent paper, fiber, or cloth materials. Additionally, the absorbent material 24 can include conventional agents that trap, stabilize or otherwise capture the moisture into a non-mobile form. The inner bag 16 further comprises a moisture resistant adhesive material 28 suitable for application to the patient's skin, where the adhesive material 28 is applied to the outer surface of the front side 18 of the inner bag 16, substantially surrounding the opening 22, without discontinuity such that a protective seal can be formed when the inner bag 16 is applied to the patient's skin.

In an embodiment the inner bag 16 is rectangular, circular, elliptical, or other suitable shape.

In an embodiment the opening 22 is rectangular, circular, elliptical, or other suitable shape.

In an embodiment the adhesive material 28 is covered by a removable release layer, such that the catheter 50 may be inserted into the inner bag 16 without adhering to the adhesive material 28.

Figure 7:
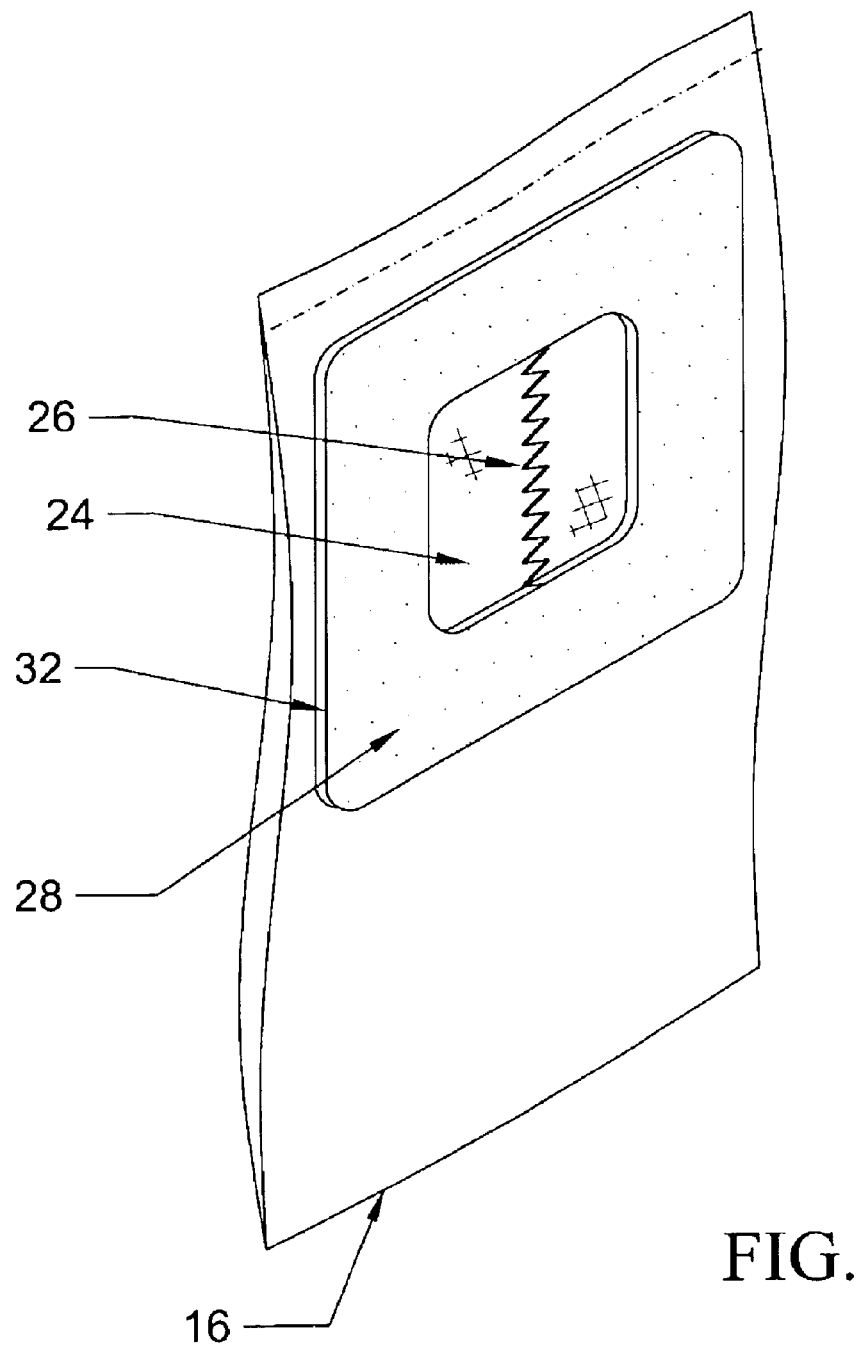
FIG. 7 depicts a perspective view of the inner bag with an annular ring.

In an alternative embodiment, as shown in FIG. 7, the inner bag 16 further comprises an annular ring 32, where the annular ring 32 is affixed about the opening 22 of the inner bag 16. The annular ring 32 is made of a flexible material capable of conforming to the surface of a patient's skin.

Figure 3:
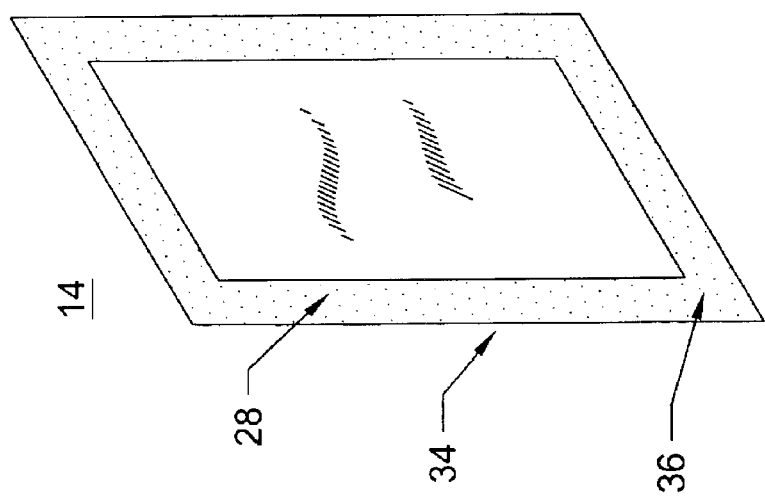
FIG. 3 depicts a perspective view of the outer cover.
Figure 6:
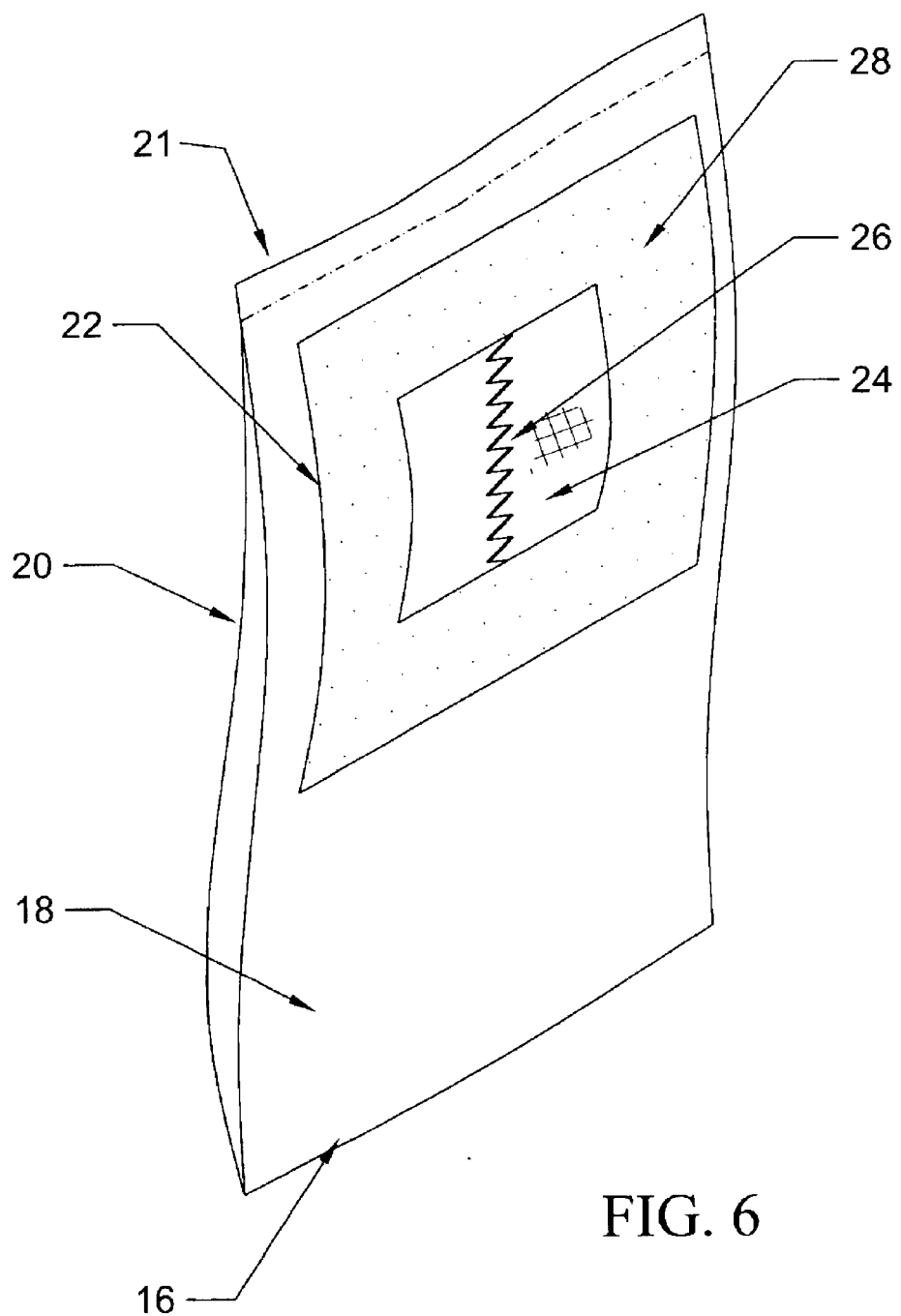
FIG. 6 depicts a perspective view of the inner bag with the absorbent material.

As shown in FIG. 3, the second protective layer 14 comprises an outer cover 34 having a peripheral edge 36 that when adhered to the patients skin, surrounds the inner bag 16. A moisture resistant adhesive material 28 suitable for application to the patient's skin is applied to the peripheral edge 36 without discontinuity such that a protective seal can be formed when the outer cover 34 is applied to the patient's skin. The outer cover 34 is sized such that the inner bag 16 is encompassed within the peripheral edge 36.

In an embodiment the second protective layer 14 is rectangular, circular, elliptical, or other suitable shape.

Figure 8:
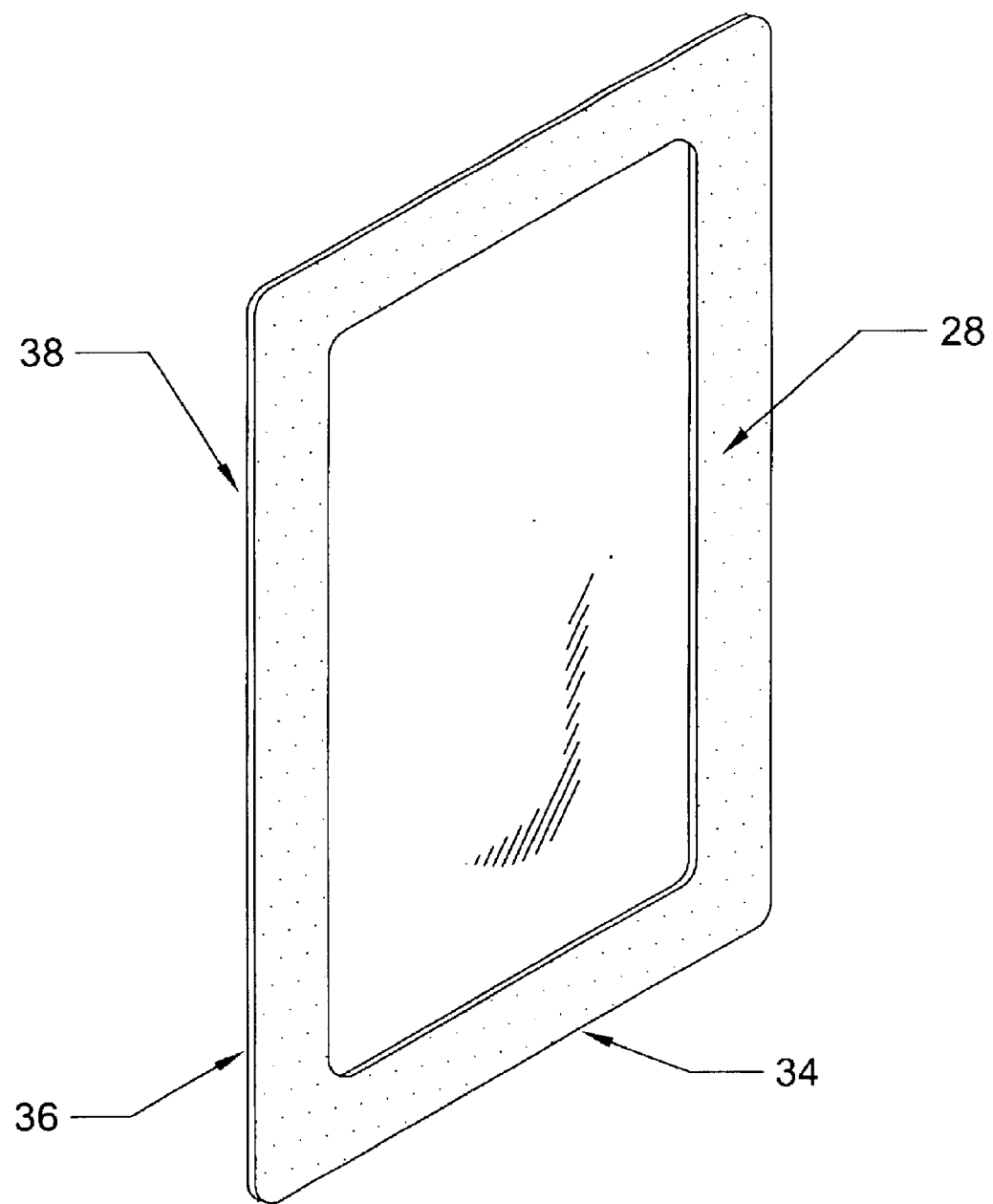
FIG. 8 depicts a perspective view of the outer cover with an annular ring.

In an alternative embodiment, as shown in FIG. 8, the outer cover 34 further comprises an annular ring 38, where the annular ring 38 is affixed about the peripheral edge 36 of the outer cover 34. The annular ring 38 is made of a flexible material capable of conforming to the surface of a patient's skin.

In an embodiment, as shown in FIGS. 1 and 2, the inner bag 16 is affixed to the outer cover 34, where the top edge 21 of the protected bag 16 is affixed to the outer cover 34.

Figure 9:
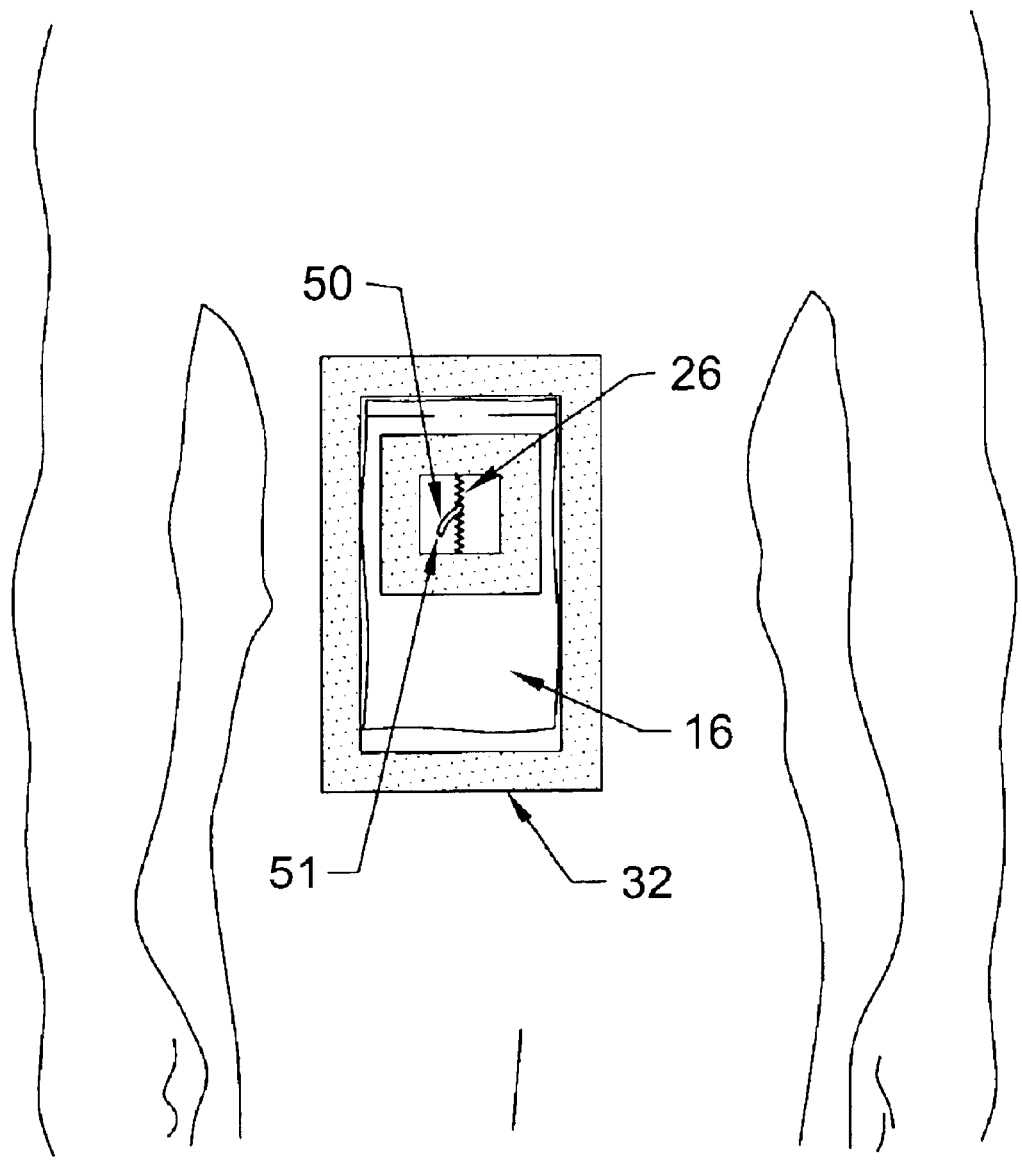
FIG. 9 depicts a perspective view of a catheter within the protective shield.

In a method of use, as shown in FIGS. 2 and 9, a catheter 50 is inserted into the inner bag 16 by inserting the proximal end 51 of the catheter 50 though the slit 26 in the absorbent material 24. The catheter 50 is drawn into the inner bag 16 until the absorbent material 24 abuts the catheter 50 exit site and surrounding area. The inner bag 16 is secured in position by the adhesive material 28 contacting with the patient's skin forming a protective seal. The outer cover 34 is positioned over the inner bag 16, such that the inner bag 16 is positioned with the peripheral edges 36 of the outer cover 34. The outer cover 34 is secured in position by the adhesive material 28 contacting the patient's skin, such that the outer cover 34 forms a protective seal about the inner bag 16, protecting the inner bag 16 from moisture, dirt, and debris.

Following are examples which illustrate procedures for practicing the invention. These examples should not be construed as limiting. All percentages are by weight and all solvent mixture proportions are by volume unless otherwise noted.

EXAMPLE 1

Catheter Protective Shield in the form of an Inner Pouch and Outer Tarp

The protective shield consists of an inner plastic pouch whose opening is surrounded by a medical grade absorbent material, which is surrounded by a medical grade adhesive that attaches to the patient. The medical grade absorbent material covering the opening of the pouch, will trap and hold fluid penetrating the adhesive barriers affording an additional level of protection in preventing fluid from reaching the inside of the pouch. The pouch is of adequate size to accept the end of a medical device existing the body. The protective shield further comprises an attached outer plastic tarp which covers the pouch, where the edged of the tarp is surrounded with medical grade adhesive, that adheres to the patient, diverting the flow of fluid away from the opening of the pouch. The protective shield is designed to be used by patients with medical devices exiting their bodies while they shower, bath, swim or perform activities where the device exist site from the body is at risk of coming into contact with excessive fluid and/or debris.

The adhesive is covered by a protective peel, allowing the patient to insert the medical device through the absorbent material, into the pouch, without the adhesive sticking to the patient, tarp, pouch, or medical device. The protective peel is removed once the medical device is inserted through the absorbent material and the pouch is adhered to the skin. Similarly, once the pouch is in position, the protective peel is removed from the tarp and the tarp is adhered to the skin, over the pouch.

The protective shield provides three layers of protection for the medical device and exit site. The first layer of protection is the tarp, directing the flow of water and/or debris away from the pouch. The second layer of protection is the adhesive on the pouch, which protects and seals the area surrounding the exit site. The third layer of protection is the adsorbent material. If water should be present in the opening of the pouch, the absorbent material will absorb it.

It should be understood that the example and embodiments described herein are for illustrative purposes only and that various modifications or changes in light thereof will be suggested to persons skilled in the art and are to be included within the spirit and purview of this application and the scope of the appended claims.

What is claimed is:

1. A protective shield for providing a protective barrier around the puncture site of an indwelling catheter comprising:
   a) an inner bag having at least one opening for placement over the catheter, wherein said opening comprises absorbent material affixed within, said absorbent material formed for receiving an exposed end of the catheter, said inner bag further comprising an adhesive substantially surrounding said opening for attachment to the skin, such that a protective seal can be formed between said inner bag and the skin; and
   b) an outer cover comprising a flexible sheet having adhesive about a peripheral edge for adhering to the skin over said inner bag such that said inner bag is sealed beneath said outer cover forming a protective seal.

2. The protective shield according to claim 1, wherein said inner bag and said outer cover are made from a flexible, fluid impermeable material.

3. The protective shield according to claim 2, wherein said flexible, fluid impermeable material is plastic, polymer, silicon, vinyl, latex, or rubber.

4. The protective shield according to claim 1, wherein said inner bag and said outer cover are made from a material substantially impervious to infectious agents.

5. The protective shield according to claim 1, wherein said inner bag comprises an annular ring integrally formed with said opening.

6. The protective shield according to claim 1, wherein said outer cover comprises an annular ring integrally formed with said peripheral edge.

7. The protective shield according to claim 1, wherein said adhesive is a medical grade adhesive for application to the skin.

8. The protective shield according to claim 1, where in said adhesive is a moisture resistant adhesive.

9. The protective shield according to claim 1, wherein said adhesive comprises a removable strip for protecting said adhesive prior to use.

10. The protective shield according to claim 1, wherein said absorbent material comprises a slit formed for receiving the exposed end of the catheter.

11. The protective shield according to claim 1, wherein said absorbent material is an absorbent paper, absorbent fiber, or absorbent cloth.

12. The protective shield according to claim 1, wherein said inner bag is affixed to said outer cover.

13. A protective shield for protecting an indwelling catheter and exit site from moisture and debris comprising:
   a) a flexible, fluid-impermeable inner bag comprising a means for receiving a proximal end of a catheter projecting through the skin, said inner bag further comprising an adhesive substantially surrounding said means for receiving the proximal end for attachment to the skin, such that a protective seal can be formed between said inner bag and the skin; and
   b) flexible, fluid-impermeable outer cover comprising means for adhering said outer cover to the skin, wherein said inner bag is sealed beneath said outer cover, such that a protective seal can be formed between said outer cover and the skin.

14. The protective shield according to claim 13, wherein said means for receiving a proximal end of a catheter projecting through the skin comprises an absorbent material.

15. A protective shield comprising:
   a) an inner bag comprising an opening and an absorbent material, wherein said absorbent material is affixed within said opening and said absorbent material is formed for receiving a proximal end of a catheter projecting through the skin, said opening comprises a means for adhering said opening to the skin, such that a protective seal can be formed between said inner bag and the skin; and
   b) an outer cover comprising a flexible sheet having a peripheral edge, wherein said peripheral edge comprises means for adhering said peripheral edge to the skin, such that a protective seal can be formed between said peripheral edge and the skin, wherein when said outer cover is adhered to the skin inner bag is sealed beneath said outer cover, within said peripheral edge.

16. A protective shield for protecting an indwelling catheter and exit site from moisture and debris comprising:
   a) a flexible, fluid-impermeable inner bag comprising a means for receiving a proximal end of a catheter projecting through the skin, said inner bag further comprising an adhesive substantially surrounding said means for receiving the proximal end for attachment to the skin, such that a protective seal can be formed between said inner bag and the skin; and
   b) an outer cover comprising means for adhering said outer cover to the skin, wherein said inner bag is affixed to and sealed beneath said outer cover, such that a protective seal can be formed between said outer and the skin.

* * * * *

UNITED STATES PATENT AND TRADEMARK OFFICE
CERTIFICATE OF CORRECTION

PATENT NO. : 6,834,652 B2
DATED : December 28, 2004
INVENTOR(S) : Sanford D. Altman Page 1 of 1

It is certified that error appears in the above-identified patent and that said Letters Patent is hereby corrected as shown below:

Title page,
Item [57], ABSTRACT,
Line 3, "shield includes" should read -- shield comprises --.

Column 6,
Line 17, "to the skin inner bag" should read -- to the skin said inner bag --.
Line 30, "said outer and" should read -- said outer cover and --.

Signed and Sealed this

Seventeenth Day of May, 2005

JON W. DUDAS
*Director of the United States Patent and Trademark Office*